United States Patent [19]

Carroll

[11] Patent Number: 5,455,285
[45] Date of Patent: Oct. 3, 1995

[54] COMPOSITION FOR TAKING AND RETAINING A DENTAL IMPRESSION

[75] Inventor: Thomas J. Carroll, Oak Ridge, N.J.

[73] Assignee: Nabisco, Inc., Parsippany, N.J.

[21] Appl. No.: 185,545

[22] Filed: Jan. 24, 1994

[51] Int. Cl.$^6$ .............................. C08K 3/32; C08K 5/01; C08L 23/20; A61K 6/10
[52] U.S. Cl. ..................... 523/109; 524/414; 524/488; 524/579; 524/437; 524/436; 524/444; 524/427; 524/451; 433/214; 426/6
[58] Field of Search ............................. 523/109; 524/488, 524/579, 414, 427, 451, 437, 444, 436; 433/214; 426/6

[56] References Cited

FOREIGN PATENT DOCUMENTS

| 0574968 | 4/1959 | Canada | 524/579 |
| 0123497 | 10/1984 | European Pat. Off. | 426/6 |

*Primary Examiner*—Paul R. Michl
*Assistant Examiner*—Andrew E. C. Merriam

[57] ABSTRACT

A gum of 5–20 wt. % polyisobutylene, 20–70 wt. % filler and 10–50 wt. % microcrystalline wax with optionally a flavorant and/or a sweetener, is flexible and soft enough to withstand repeated severe flexing yet can take and retain a dental impression after a single bite. The gum is free of crystallizable ingredients such as bulk sweeteners and therefore exhibits outstanding storage stability.

5 Claims, No Drawings

COMPOSITION FOR TAKING AND RETAINING A DENTAL IMPRESSION

FIELD OF THE INVENTION

The present invention relates to an impression material and a method of using the impression material to make dental impressions.

BACKGROUND OF INVENTION

Various types of materials for making dental impressions are known, but they are relatively inconvenient to use and can be unpleasant to the user and patient.

Dental plaster is one material used to make dental impressions. Gypsum, which is widely distributed naturally as calcium sulfate dihydrate ($CaSO_4.H_2O$), has been used since 1844 in the production of dental plaster.

To form an impression using dental plaster, the gypsum is ground and subjected to temperatures of 110° C.–120° C. to provide large and porous crystals. These crystals typically require a 2:1 powder-gauging water ratio for proper consistency.

However, the preparation of an impression using such dental plaster is time-consuming and messy. Immediately prior to the time it is desired to make an impression, the gypsum crystals are mixed with an appropriate amount of water to produce a thin, fluid slurry. Subsequently, to form the impression or negative, the plaster slurry is placed in a tray, inserted into the mouth, pressed in place against the area in question, and held still until the plaster hardens at which time the plaster impression is removed from the mouth.

Generally, the impression plaster is used to obtain an impression or negative of the hard and soft tissues of the mouth. After the plaster impression is removed, model plaster may be poured into the impression to produce a cast (positive). A satisfactory impression plaster has a setting time from about 2.5–5.5 minutes, a setting expansion at 2 hours less than 0.15%, and a compressive strength at one hour between 8265.5–8845.5 psi.

Wax is another material used to make dental impressions. The wax compositions for dental usage are usually compounded in conventional melting and blending equipment and in a manner that avoids the degradation of wax properties. While soft, low melting, plastic waxes are suitable, when a complete impression is desired, hard high-melting, rigid base waxes are used with successively softer wax additions to build the complete impression.

Although the exact formula of an impression wax is typically a trade secret, several different components have been identified in the wax depending upon the intended use of the impression. For instance when a negative cast of the mouth structure is desired, paraffin, ceresin, vegetable wax, rosin, mastic gum, and spermaceti have been identified as components used in the impression wax.

When an impression wax is used to establish tooth articulation, i.e., the occlusion or horizontal relationship of the lower jaw to the upper jaw, high-flow, low-melting paraffins, microcrystalline waxes and resins have been identified as components of the impression or bite wax.

When an impression wax is used to detect tooth interference and high spots or improper fit of dentures bases, the wax is very soft and salve-like (i.e., a pressure indicating paste) and painted onto the tissue side of an impression or denture. When situated in the mouth the paste is forced out of the area having contact with the tissue.

At the time impression wax is used to obtain an impression, the wax may need to be heated. Alternatively, impression waxes, which are plastic and moldable at mouth temperature, must be cooled below mouth temperature to obtain a nonelastic mass which retains the impression. Thus, similar to impression plaster the preparation and use of impression waxes can be cumbersome and possibly dangerous to the patient, since the wax may be heated too much and burn the inside of the mouth or may not be soft enough to create an impression with an easy bite and thereby cause an injury to the mouth, teeth or jaw.

Impression materials based on reversible hydrocolloids (agar), irreversible hydrocolloids (alginates), combinations of agar and alginate, and to a lesser extent, oxide-eugenol cements, have also been employed to make dental impressions.

Agar-based impression materials are thermally reversible, aqueous gels that become viscous fluids in boiling water and set to an elastic gel when cooled below 35° C. Such material is typically used to obtain impressions of inlay and crown preparations and gingival areas by filling the preparation or area with the impression material injected from a hypodermic syringe.

To form agar-based impression material, about 6–12% agar is generally used with a 75–80% water content. Fillers such as zinc oxide and clays may be incorporated as well as other additives such as boron incorporated as well as other additives such as boron compounds (borax, calcium metaborate and organic borate compounds), waxes or fatty acids, emulsifying agents and plaster-accelerating agents (i.e., potassium sulfate, magnesium sulfate and zinc sulfate). To remain stable in storage agar impression materials must be free of salts or additives that crystallize and salt out, degrade the complex molecule or induce syneresis in the agar gel.

Moreover, prior to insertion or injection into the mouth, agar-based materials require time consuming preparation which includes cooling the material to produce a gel. After a gel has been obtained and inserted in the mouth or over an area for which an impression is desired, a setting time is required to elapse before the gel can be removed.

Potassium or sodium salts of alginic acid are useful alginate impression materials. Alginate-based irreversible hydrocolloid impression materials, which constitute chemically reactive mixtures, are supplied as a dry powder which is mixed with water to form a viscous but slightly fluid mass (gel or paste). In use the gel or paste is placed over the area of which an impression is desired and allowed to set (about 1–4 minutes) to provide a strong, tough elastic gel. The impression is removed in a swift motion to minimize any tearing or distortion.

However, the agar- and alginate-based impression materials lack dimensional stability with any loss or gain of water. Consequently, improved systems are sought.

Accordingly, nonaqueous, polysulfide-, condensation silicone-, addition silicone- and polyether-based systems have also been employed as impression materials.

Polysulfide impression materials also tend to be messy and cumbersome in use since polysulfide materials are generally supplied as a two-part paste system—a polysulfide-containing, liquid polymer base and a setting-agent paste (i.e., lead peroxide). When the liquid polymer base and paste are mixed together (in approximately equal amounts) a homogeneous, streak-free mass (elastic solid) is provided. The mass is transferred to a tray which is then placed over the area of interest and held motionless (for about 5–10 minutes) until the rubber has set.

The polysulfide base material ordinarily contains 50–80% of the polyfunctional mercaptan and, additionally, a filler (i.e., calcium carbonate, alumina, silica), diluents, modifying agents, retarding agents and buffering agents.

The setting agent paste typically comprises alkalies, sulfur, metallic oxides, metallic peroxides, organic peroxides or metal-organic salts. The paste can also include a diluent, filler, buffering agent or other modifier.

The silicone impression material systems are nontacky and can be wiped away from instruments or hands at any stage of the mix or set. However, the silicone systems are moisture sensitive and subject to deterioration when exposed to the atmosphere. The silicone impression materials provide impressions in a manner similar to the polysulfide systems.

Condensation silicone impression materials are two part systems based on hydroxyl-terminated polydimethylsiloxane. The systems can be either two pastes or a paste-liquid catalyst which must be mixed outside of the mouth. The silicone is a viscous liquid to which colloidal silica or micronized metal oxides are added to provide a paste. The catalyst part of the system can be a tetraalkyl silicate containing 50% ethoxy group, such as tetraethyl orthosilicate and 1–2% of an organic tin activator, which is not necessarily desirable for placement in the mouth.

Addition siloxane impression materials are supplied in an awkward two-paste systems wherein one paste contains low molecular weight silicone with terminal vinyl groups and reinforcing filler and the second paste contains a hydrogen-terminated siloxane oligomer, filler and chloroplatinic acid catalyst. Mixing the two pastes provides a cross-linked elastomer. Since hydroxyl-containing silicones evolve hydrogen, palladium has been added to some formulations.

Polyether impression material is also supplied in a two-paste system. Typically one paste contains a branched polyether molecules having a main chain of an ethylene oxide-tetrahydrofuran copolymer and a second paste containing an aromatic sulfonate ester catalyst. When mixed together cross-linking is brought on by cationic polymerization via the imine end groups. The polyether impression system is used similar to the silicone and rubber systems. Although setting time is less than 2.5 minutes, the polyether elastomer is more difficult to remove from the mouth, will readily tear, and has poor dimensional stability in water.

Each of the impression materials described above requires mixing of different materials and/or temperature fluctuation to provide the impression material which will be used to provide an impression of the teeth. Thus, there remains a need for a formulation of impression material having a fairly stiff yet malleable consistency which is simple to use and does not require preparation time or setting time. There is a particular need for impression materials which are easily handled and accurately reproduce or register the dimensions, surface details, and interrelationship of the teeth.

There is also a need for an impression material which can retain its desirable flexibility, and its capability to take and retain a dental impression, for a prolonged period of time without suffering a change in these properties during storage.

SUMMARY OF THE INVENTION

The present invention satisfies these needs, while exhibiting the advantageous properties enumerated herein.

The present invention is a chewing gum which comprises about 5 to about 20 wt. % of polyisobutylene having a molecular weight of about 40,000 to about 125,000; about 20 to about 70 wt. % of an inorganic filler; and about 10 to about 50 wt. % of microcrystalline wax. The gum may further comprise an optional flavoring component and/or an optional sweetening component, but the gum is free of any sweetener, or any other component, that is capable of crystallizing in, or from, the gum. Such crystallizable components generally comprise bulk sweeteners.

The gum of the present invention is flexible, and retains its flexibility for a long period of time. It is so flexible that it can be folded back on itself without tearing or breaking. The gum is also soft enough to receive a dental impression, and stiff enough to maintain such an impression without sagging.

DETAILED DESCRIPTION OF THE INVENTION

The gums of the present invention comprise an elastomer. The preferred elastomer is polyisobutylene having a molecular weight of about 40,000 to about 125,000, which is employed in amounts from about 5 to about 20 wt. % of the gum.

The gums in accordance with the present invention further contain an inorganic filler. The filler is preferably selected from the group consisting of dicalcium phosphate anhydrous, amorphous hydrated silica, dicalcium phosphate dihydrate, aluminum hydroxide, magnesium hydroxide, alumina, aluminum silicates, calcium carbonate, talc, and combinations thereof. The preferred filler is dicalcium phosphate anhydrous. The filler may be present in the gum in amounts from about 20 to about 70% by weight of the final gum. In a preferred embodiment the amount of dicalcium phosphate anhydrous is about 30% by weight of the gum.

The filler provides desired bulk, texture and mouth feel to the product. It is particularly noteworthy that the gum undergoes no loss or separation of the filler from the product.

The gums of the present invention also contain a wax having a softening point between about 165° C. and about 198° C., preferably between about 165° C. and about 180° C. Microcrystalline wax is the preferred wax to employ to obtain the desirable texture and consistency properties. This wax reduces the tackiness of the gum without significantly reducing cohesivity thereof. It also improves the ease of biting into the material, and helps the gum to form and hold a distinct, firm shape wherever the gum is bitten into. This wax is generally employed in amounts of about 10% by weight up to about 50% by weight of the gum.

The gums of this invention may also contain a flavorant. Suitable flavorants include both natural and artificial flavors and mints, such as oil of peppermint, menthol, oil of spearmint, vanilla, oil of cinnamon, oil of wintergreen (methyl salicylate), and various fruit flavors, including but not limited to lemon oil, orange oil, grape flavor, lime oil, grapefruit oil, apple, apricot essence, and combinations thereof. The flavorings are generally utilized in amounts that will vary depending upon the individual flavor. Optionally, a small amount of a vegetable oil or equivalent material can be added to the flavor oil when it is desired to lessen any overly strong impact of the flavor. The flavorants are generally utilized in amounts that will vary depending upon the individual flavor, and may, for example range in amounts of 0.5% to about 3% by weight of the final composition product.

The present invention contemplates the optional inclusion in the impression material of a sweetener component which may comprise any one or more intense sweeteners known in the art. However, the bulk sweeteners which are generally known for use in chewing gums are not acceptable in the gums of the present invention. Thus, sweeteners may be chosen from the following non-limiting list, which includes saccharin and its various salts such as the sodium or calcium salt; cyclamic acid and its various salts such as sodium salt; free aspartame; dihydrochalcone sweetening compounds; glycyrrhizin; Stevia rebaudiana (Stevioside); monellin, thaumatin, and 1,6-dichloro-1,6-dideoxy-β-D-fructofuranosyl -4-chloro-4-deoxy-d-D-galactopyranoside (Sucralose). Also contemplated as a sweetener is the sugar substitute 3,6-dihydro-6-methyl-1 -1,2,3-oxathiazin-4-one-2,2-dioxide, particularly the potassium (Acesulfame-K), sodium and calcium salts thereof as described in German Patent No. 2,001,017.7.

Sweeteners to be avoided in the gums of the present invention include sugars such as sucrose, glucose, corn syrup, dextrose, invert sugar, fructose and mixtures thereof; neosugar, polydextrose, and sugar alcohols such as sorbitol, sorbitol syrup, mannitol, xylitol, isomaltitol, lactitol, maltitol, and the hydrogenated starch hydrolysate (also known as Lycasin) which is described in U.S. Pat. No. Re. 26,959.

As indicated, products within the scope of the present invention may include no sweetener at all. If sweetener is included, the amount of sweetener is effective to provide the desired degree of sweetness, generally 0.001 to 0.5 wt. % of the final product.

Colorants can be present in the gums of the present invention. Examples include the pigments such as titanium dioxide and other dyes suitable for food, drug and cosmetic applications known as F. D. & C. dyes, and the like. The materials may be incorporated in amounts of up to about 6% by weight, preferably under about 1% by weight.

Gums in accordance with this description have been found to exhibit numerous useful properties.

The gums are very flexible. By this is meant that a conventional-sized stick of gum in accordance with this invention can be folded, even doubled over on itself, without breaking, tearing, or even forming a noticeable score line. The gums are also very soft, as shown by the same capability and by the fact that even repeated severe flexings do not cause the gum to break or tear.

The gums also retain their flexibility and softness for prolonged periods of time, even on the order of months. This property enables commercial gum products embodying the present invention to be purchased and stored in inventory or on a store shelf for a long time without the need to rotate the stock to keep it fresh. This property, termed "storage stability", is believed to be due to the absence of ingredients which could crystallize in, or from, the gum. Most notable of such crystallizable ingredients absent from the gums of the present invention are bulk sweeteners such as sugars and other carbohydrate-derived sweeteners.

The gums according to the present invention also have the ability when bitten upon to take a sharp, well-defined impression of the teeth, and the ability when subsequently removed from the mouth to hold that impression without perceptible shift of the dimensions of the impression (i.e., without "sagging"). The combination of pronounced flexibility and softness, with pronounced ability to hold a dental impression without sagging, is believed to be particularly unexpected in that such properties are generally considered to be somewhat incompatible with each other.

The gums of the present invention, if desired also are excellent bubble gums in that they enable the user to generate large, firm, long-lasting bubbles.

The gums in accordance with the present invention can be formulated with conventional equipment. Thus, preferably, the gum components are softened together by heating and then mixed together, and the mixture is stirred together for a time sufficient to insure a homogeneous mass. The mass is formed into slabs from which individual block-shaped or stick-type pieces can be cut using technology familiar to those skilled in the art.

The gums of the present invention can be used in several ways. One way is to obtain a dental impression to enable measurement or observation of the dimensions of a person's mouth, or the relative positioning of the teeth. With this objective, a stick-sized piece of the gum is curved to conform to the general contours of the teeth; or, preferably, the stick is simply folded over on itself along a line, roughly in the center of the stick, which is at an angle of about 45° to the long axis of the stick. Such a fold forms the stick into a V-shape. The piece is then placed into the mouth, and the mouth is closed onto the gum thereby providing an imprint or impression of the teeth therein. The impression is retained in the gum which is then removed from the mouth. Generally, the impression will be created by a single bite down on, but not through, the gum which is ready for immediate removal upon reopening of the mouth. The advantageous properties of this gum permit use of the dental impression thus created to measure or observe the size and location of the teeth in the mouth. For instance, one may discern from the impression the appropriate size of an athletic mouthguard for the person.

It is a significant advantage that the gums of the present invention incorporate ingredients which are readily available and inexpensive thereby providing a gum which can be used as a dental impression material which is uncomplicated, non-messy and inexpensive.

The impression material is easily removed due to its nontacky texture and does not stick to the teeth or gums even if wet.

Unlike many of the prior art impression materials, the use of the gums of the present invention as an impression material involves no preparation time by the user. The user simply unwraps the gum and uses it. There are no messy pastes or gels. No setting time and minimal insertion time are required. Furthermore, there is no need to heat and/or cool the gum either before or after the desired impression is obtained. Not a single additional instrument or even a tray is required in the present method.

Stick-type pieces of gum useful in this application are generally approximately 4–5 inches in length, 0.25–1.0 inch in width and 0.15–0.5 inches in height. In a particularly preferred embodiment the impression material is about 4.5 inches in length, 0.5 inches in width and 0.25 inches in height.

Another way to use the gums of the present invention is to form a piece of gum more in the shape of an elongated block, having a larger height, on the order of 0.5–1 inch, than the sticks described above.

The block is formed into a general U-shape in which it can contact all the subject's upper and lower teeth. Then, the subject bites into the gum sufficiently to form an impression of the upper and lower teeth. The block needs to be high enough that the teeth sink into the gum up to the gum line, while retaining a layer of gum between the upper and lower teeth. When the gum block is then removed from the mouth, a medication or health-sustaining preparation such as a topical fluoride composition can be placed in the space created by the impression of the upper and lower teeth. The preparation can be liquid, gel, or paste-like. Of course, a more viscous preparation is preferred for placement in the impression space formed by the lower teeth. Then, the gum is reinserted into the mouth and the subject bites carefully onto it. The teeth reoccupy the spaces they previously created, and as the teeth are gently pressed into those spaces the preparation is spread against, around, and between the teeth. After a suitable interval, the gum is again removed and the teeth are, if desired, rinsed off.

EXAMPLE

A preferred example of gum in accordance with the present invention is set forth in the following table:

| Component | Amount (Wt %) |
| --- | --- |
| Polyisobutylene-C | 50.00 |
| Dicalcium Phosphate Anhydrous | 30.00 |
| Microcrystalline Wax 2305 | 19.39 |
| Peppermint Oil | 0.50 |
| Saccharin, Sodium | 0.10 |
| FD & C Blue #1 Aluminum Lake | 0.01 |
| Total: | 100.00 |

What is claimed is:

1. A gum useful to take and retain a dental impression, wherein the gum consists of:

(a) about 5 to about 20 wt. % of polyisobutylene having a weight average molecular weight of about 40,000 to about 125,000;

(b) about 20 to about 70 wt. % of an inorganic filler;

(c) about 10 to about 50 wt. % of microcrystalline wax having a softening point of about 165° C. to about 198° C.; and (d) optionally, one or more ingredients selected from the group consisting of flavorant, sweetener which is not crystallizable in or from said gum, and colorant;

wherein said gum is free of substances crystallizable in or from said gum.

2. The gum according to claim 1, wherein said inorganic filler is selected from the group consisting of amorphous hydrated silica, dicalcium phosphate dihydrate, dicalcium phosphate anhydrous, aluminum hydroxide, magnesium hydroxide, alumina, aluminum silicates, calcium carbonate, talc, and combinations thereof.

3. The gum according to claim 1, wherein said inorganic filler is dicalcium phosphate anhydrous.

4. The gum according to claim 1, wherein said flavorant is selected from the group consisting of peppermint oil, menthol, cinnamon oil, spearmint oil, vanilla, wintergreen oil, lemon oil, orange oil, grape, lime oil, grapefruit oil, apple, apricot essence, and mixtures thereof.

5. The gum according to claim 1, wherein said sweetener is selected from the group consisting of saccharin, salts of saccharin, cyclamic acid, salts of cyclamic acid, aspartame, dihydrochalcones, glycyrrhizin, Stevia rebaudiana, monellin, thaumatin, Sucralose, Acesulfame, salts of Acesulfame, and mixtures thereof.

* * * * *